(12) United States Patent
Groitzsch et al.

(10) Patent No.: US 6,448,462 B2
(45) Date of Patent: Sep. 10, 2002

(54) MEDICAL BANDAGING MATERIAL

(75) Inventors: Dieter Groitzsch, Hirschberg; Gerhard Schaut, Hemsbach, both of (DE)

(73) Assignee: Firma Carl Freudenberg, Weinheim (DE)

( * ) Notice: Subject to any disclaimer, the term of this patent is extended or adjusted under 35 U.S.C. 154(b) by 0 days.

(21) Appl. No.: 09/770,537

(22) Filed: Jan. 26, 2001

(30) Foreign Application Priority Data

Feb. 28, 2000 (DE) .......................................... 100 09 248

(51) Int. Cl.$^7$ ................................................. A61F 13/00
(52) U.S. Cl. ............................ 602/45; 602/43; 602/42; 602/41
(58) Field of Search ............................ 602/41, 42, 43, 602/53, 45; 428/290, 296, 288, 373, 364, 349, 347, 516, 910; 156/62.2, 209, 278

(56) References Cited

U.S. PATENT DOCUMENTS

| 4,630,603 A | | 12/1986 | Greenway | |
| 4,950,282 A | | 8/1990 | Beisang et al. | |
| 5,011,492 A | | 4/1991 | Heimerl et al. | |
| 5,540,992 A | * | 7/1996 | Marcher et al. | ............ 442/334 |
| 5,585,172 A | * | 12/1996 | Barsotti | ....................... 442/361 |
| 5,679,190 A | | 10/1997 | Riedel et al. | |
| 5,883,787 A | * | 3/1999 | Reier | .......................... 361/752 |

* cited by examiner

Primary Examiner—Michael A. Brown
Assistant Examiner—Lalita M Hamilton
(74) Attorney, Agent, or Firm—Kenyon & Kenyon

(57) ABSTRACT

A medical bandaging material made of a microfilament nonwoven fabric with a mass per unit area of 30 to 150 g/m$^2$ and a tear strength of >40 N/5 cm, the nonwoven fabric being made of continuous multicomponent filaments, melt-spun, stretched, and directly laid down to form a nonwoven fabric, having a titer of 1.5 to 5 dtex, and the continuous multicomponent filaments, after optional prebonding, being split, at least to the extent of 80%, into continuous microfilaments having a titer of 0.01 to 1.0 dtex and bonded.

17 Claims, 1 Drawing Sheet

MEDICAL BANDAGING MATERIAL

BACKGROUND OF THE INVENTION

1. Field of the Invention

Figure 1:
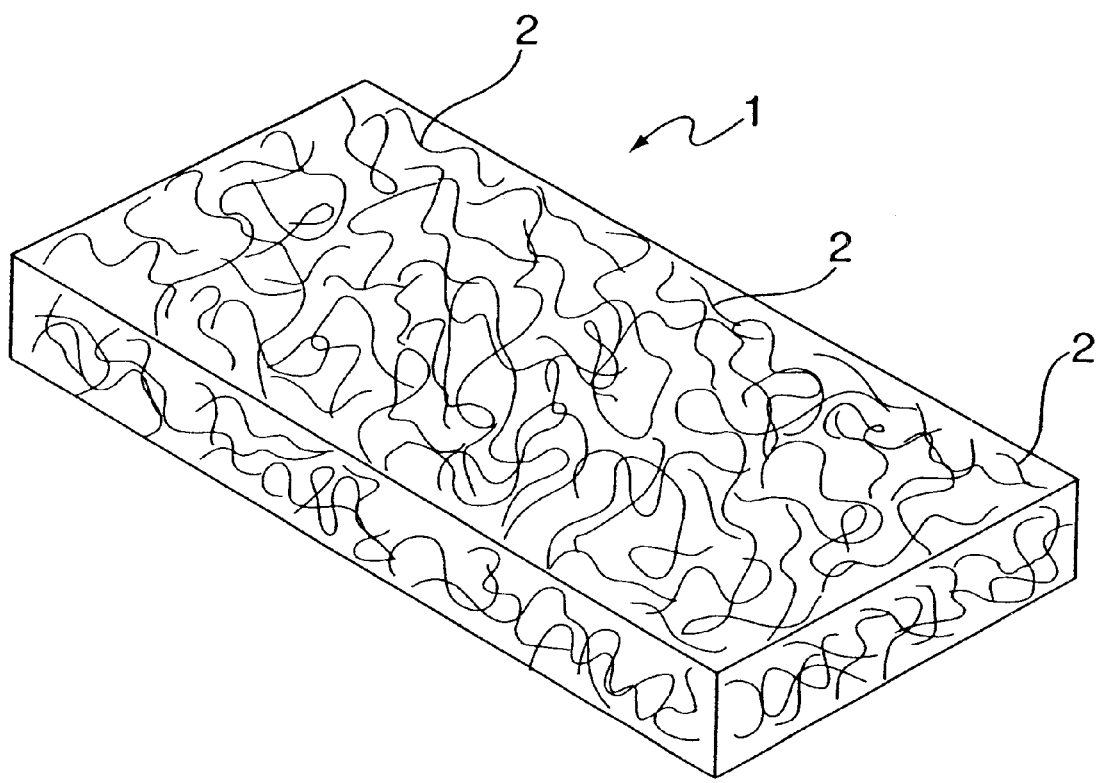

The present invention relates to a medical bandaging material.

2. Description of Related Art

Depending on the size and kind of the wound or injury, plasters with and without pads, compresses or bandages are used for medical bandaging materials. In such an application, the materials used to promote the healing process must not have any barrier effect against water vapor or the gases liberated by the healing process, such as carbon dioxide. In particular, in addition to having a high resistance to abrasion, plasters are expected to have a surface which repels dirt and has high tactility, i.e. has a nubuk leather kind of touch, as well as being free of splits and of fuzz.

From the documents U.S. Pat. No. 4,630,603, U.S. Pat. No. 4,950,282, U.S. Pat. No. 5,011,492 and U.S. Pat. No. 5,679,190 medical bandaging materials are known whose backing material is made of a nonwoven fabric. These materials have the problem, especially when they are coated with a pressure sensitive adhesive with great adhesive strength to human skin, that they tend to having the nonwoven fabric layers delaminate or the fibers leach out. This would make taking them off more difficult when changing bandages.

SUMMARY OF THE INVENTION

The object of the present invention is to set forth a medical bandaging material having high resistance to abrasion, low soilability, a high tactility, suppleness and adaptability to body shapes and movements, high gas and water vapor permeability, as well as no tendency to nonwoven fabric layer splitting.

DETAILED DESCRIPTION OF THE INVENTION

According to the present invention, the object is attained by using a medical bandaging material made of a microfilament nonwoven material with a mass per unit area of 30 to 150 g/m2 and a tear strength of >40 N/5 cm, the nonwoven fabric consisting of continuous multicomponent filaments with a titer of 1.5 to 5 dtex which are melt-spun, stretched and directly laid down to form nonwoven fabric, and the continuous multicomponent filaments, if necessary after prebonding, being, at least to the extent of 80%, split and bonded to continuous microfilaments with a titer of 0.01 to 1.0 dtex. The medical bandaging materials do not show nonwoven fabric layer delamination, and have water vapor permeability of at least 400 g/m2 and per 24 h.

The medical bandaging material is preferably one in which the nonwoven fabric has a mass per unit area of 40 to 120 g/m2 and consists of continuous multicomponent filaments with a titer of 1.5 to 3 dtex, which are melt-spun, aerodynamically stretched and directly laid down to form a nonwoven fabric, and the continuous multicomponent filaments, if necessary after prebonding, being, at least to the extent of 80%, split and bonded to continuous microfilaments with a titer of 0.05 to 0.5.

Furthermore, a particularly advantageous medical bandaging material is one in which the continuous multicomponent filament is a continuous bicomponent filament, consisting of two incompatible polymers. Such a continuous bicomponent filament is composed of polyesters, such as polyethylene terephthalate, polybutylene terephthalate or polytetramethylene teraphthalate together with a polymer incompatible with these, such as polypropylene, polyethylene, polyamide 6, polyamide 6.6, or a thermoplastic elastomer (TPE). For extremely soft, nonelastic bandaging materials, a nonelastic polymer and a TPE are used for the polymer pairing, as, for instance, a polyester elastomer and a polyamide 6.6. For extremely soft, highly stretchable elastic medical bandaging materials, a polymer pairing of two thermoplastic elastomers is used, as, for instance, a polyester elastomer with a styrene-butadiene-styrene block copolymer. Furthermore, for rigid, not very stretchable medical bandaging materials, a polymer combination of nonelastic polymers, so-called thermoplastic nonelastomers (TPNE) and thermoplastic elastomers is produced. In the polymer pairing TPNE/TPE, the lower melting, or rather lower softening component is used to produce at least partial-surface connections of the filaments of the higher melting component. The difference in melting point or adhesion temperature between TPNE and TPE is at least 10° C., and preferably at least 30° C. For the binding procedure, known methods such as directed or circulating hot air currents, hot calendering or ultrasound welding can be used.

Especially advantageous also is a medical bandaging material in which the continuous multicomponent filaments have a cross-section with an orange-like multisegment structure, the segments, in alternating sequence, each including one of the two incompatible polymers and/or a "side-by-side" structure. The medical bandaging material has a high water vapor permeability index as well as a humidity absorption capacity, so that, if necessary, one can do without the pad when using it as a plaster. The lower or upper sides of the medical dressing do not have to have the same resistance to mechanical abrasion in a dry or damp condition. To improve the resistance to abrasion and to achieve a superficially foil-like surface of the upper side, which furthermore has a microporous structure, the medical bandaging material is bonded and smoothed off by being pressed against a smooth, heated roll.

In addition, the medical bandaging material is one in which the two sides of the bandaging material have a different segment structure. This raises the absorption capability of the bandaging material. The absorption capability can also be improved by a different degree of entanglement of the fibers among one another. For this, water jet bonding is performed on the upper and lower side of the medical bandaging material with different pressures, so that a greater integrity of the upper and lower sides comes about. However, the intensity of entanglement, even at the weakest cross-sectional regions, is so strong, that delamination nonwoven fabric layers under wet or dry conditions is completely prevented. For use of the bandaging material as a plaster, the underside, on which the adhesion material layer is applied, is preferably not smoothed off, since a little roughness makes for better anchoring of the adhesive material. The continuous bicomponent filaments of the medical bandaging materials, before splitting, can also be treated by crimping, with methods known per se, with the crimping possibly being two-dimensionally flat, e.g. zigzag-shaped or spiral-shaped.

Especially advantageous is a medical bandaging material, in which at least one of the incompatible polymers, forming the continuous multicomponent filaments, contains amounts up to 10% by weight of additives such as dyestuffs, permanently acting antistatics, fungicides, bactericides, softeners, stabilizers, wetting and parting agents, optical brightening agents, additives influencing spinning character or melt fusion, as the case may be, and/or additives influencing hydrophilic or hydrophobic properties. Depending on the type of application, the specific requirements can thus be fulfilled. Medically effective additives are chosen for this in such a way that they migrate to the fiber surface, either immediately after being extruded or after storage, and there become more concentrated as well as capable of being given off to the surroundings. The additives influencing the physical properties of the fibers are preferably chosen so as to be statistically distributed constantly in time over the entire microfiber cross-section.

The method for producing a medical bandaging material preferably provides that the continuous multicomponent filaments are melt-spun, stretched and directly laid down to form nonwoven fabric, a prebonding process is optionally carried out and the nonwoven fabric is bonded by the use of high pressure fluid jets, and at the same time split into continuous microfilaments with a titer of 0.01 to 1.0 dtex. Medical bandaging materials produced in this manner have a soft touch, high resistance to abrasion, and a water vapor permeability of at least 400 g/m2 and per 24 h, but preferably 800 g/m2 and per 24 h.

The method for producing medical bandaging materials preferably consists in having the bonding and splitting of the continuous multicomponent filaments take place so that the nonwoven fabric, prebonded if necessary, has applied to it high pressure fluid jets once from each side. By choosing the number of high pressure fluid jets in the treatment, and the pressures set for it, one can set the desired gradient of the entanglement intensities, and with that, the absorption capability.

Preferably, the method for producing medical bandaging materials is also one in which the coloring of the continuous multi-component fibers is performed by spin dyeing. Particularly in the case of plasters, the medical bandaging material can be adapted colorwise, within certain limits, to the skin color of the patient, and dyed white, beige or dark brown. Alternatively to this, the dye can also be printed on the upper side of the bandaging material.

Another preferred method for producing a medical bandaging material is one in which two spinning beams are used, of which one produces a continuous multicomponent filament with a "pie" segment structure and the other with a "side-by-side" structure. This material demonstrates good absorption capability, especially when used as bandaging material without a pad.

The medical bandaging material is used preferably for producing plasters for the flat covering of small-area damage to the skin. For this purpose, the material is equipped to be hydrophobic, dirt-repellent and possibly also alcohol-repellent, at least on the side without adhesive applied to it. This occurs preferably because at least one of the two continuous microfiber filaments has the aforesaid properties. To increase dirt repellent and alcohol repellent properties, fluorocarbon resin can be added to at least one of the raw material polymers. Alternatively, application is possible by full bath impregnation, coating, printing, padding one side or spraying, preferably with aqueous dispersions. For economic reasons, the so-called wet-on-wet full bath impregnation is especially preferred. This makes it possible to do without intermediate drying to remove dampness remaining on the goods after the water jet treatment and its extraction. Wet-on-wet impregnation is a method understood to mean that the damp goods are furnished with the finishing agent without intermediate drying. This involves further measures which prevent dilution of the liquor in the padding machine trough in the case of full bath impregnating in a padding machine. This occurs advantageously since the concentration or rather the solid content of the finishing agent steadily pumped into the padding machine trough is higher than the liquor in the trough. A textile dye and/or a pigment dye can also be added to the finishing agent. In the case of a pigment dye, an aqueous plastic dispersion is added for fixing it. A combination of a nonionic fluorocarbon resin dispersion/emulsion and disperse dyestuffs, which can be applied in the Thermosol Process, has proven successful for simultaneously making water-repellent and dyeing the polyester fibers in medical bandaging material according to the present invention.

To produce a plaster, the nonwoven backing made of continuous microfilaments is coated with a contact adhesive, which, even at skin temperature of the patient, permits it to be affixed to the skin with light contact pressure. Film extrusion, printing, powdering, flocking, spinning or spraying are suitable processes for applying the adhesive.

Preferably, a full-surface adhesive coating is applied with a bonding adhesive which has a high permeability to water vapor, oxygen and carbon dioxide.

Preferably, the water vapor permeability of the nonwoven fabric coated with adhesive is at least 400 g/m2 and per 24 h, but preferably at least 800 g/m2 and per 24 h.

By preference, the adhesive is applied dissolved in an organic solvent or dispersed in water. Alternatively, the adhesive can also be applied via so-called transfer coating ("reverse coating"), first being applied to a "release medium" (release paper), and then transferred together with it to the microfilament nonwoven fabric. Furthermore, a release paper-free application of bonding adhesive on the microfilament nonwoven fabric is also advantageous when the latter bears a release finishing on the side turned away from the adhesive.

Mainly, such an adhesive release finishing consists of means for making water-repellent, which are known per se, as, for instance, fatty acid-modified melamine resins and their blends with paraffins, heavy metal salt-linked paraffins, fluorocarbon resins, silicones or silicone elastomers, or combinations of the aforesaid products. The medical bandaging material can be used in the form of narrow rolls, with or without nonwoven fabric paper. For covering secreting wounds, an absorbing body for taking up secretion and blood is added on part of the surface of the side coated with bonding adhesive. The absorbing body, hereafter called a pad, is covered on the wound side, or skin side, with a porous, smoothed-off nonwoven fabric, a perforated foil or a plastic net for preventing bonding with the wound or for preventing traumatizing the wound when the bandaging material is removed. This covering can wind around the absorbing pad, so that even the edge cut of the suction cushion is enwrapped and fixed on the adhesive layer. Or it can simply lie on the pad and be connected with it by mechanical or adhesive binding techniques.

Advantageously, the pad is impregnated with germicidal or germ growth inhibiting ingredients. The pad can be made of an absorbent woven fabric, a knitted fabric, a nonwoven fabric, a nonwoven fabric-thread combination or an open-cell foam material.

By preference, the pad is made of hydrophilic or hydrophilized fibers, of foam materials or of gels, such as alginate, carboxymethylated lyocell fibers or of chitosan.

In a further preferred embodiment, the bandaging material is one that is used to produce active content plasters. By encapsulating medically active substances, or by impregnating the pad with medically active substances, active content plasters can be produced which have a storage effect, i.e. a long lasting application of the active substance.

In a further preferred embodiment, the medical bandaging material is one that is used to produce bandages. Advantageously, the bandaging material is treated with a mechanical softening process. Particularly favorable is stretching the nonwoven fabric in the longitudinal and/or transverse directions, preferably in the transverse direction, i.e. at a 90° angle to the water jet path. This raises the elasticity of the bandaging material.

In yet another preferred embodiment, the medical bandaging material is used to produce wound compresses. By adding binding materials, correspondingly stiff wound compresses can be obtained. Furthermore, both for plasters and wound compresses an additional layer of staple fiber can be applied. This raises the absorption capability of the bandaging material.

The choice of raw material components, for the medical bandaging material according to the present invention, is made according to the sterilization requirements. Sterilization is preferably done by irradiation, wherein, by using polypropylene, the latter is provided with appropriate stabilizers against degradation.

The invention is elucidated further by the following examples:

EXAMPLE 1

Using known technology, continuous bicomponent filaments were spun from the components polyethylene terephthalate and polyamide 6.6, which, after leaving the nozzle plate and before being laid down on a lay-down conveyor, were jet-quenched with a directed air current and stretched to fine filaments. The laying down of the continuous filaments to form a fabric was carried out in such a way that approximately the same mechanical tenacity resulted in the machine running direction as in the transverse direction thereto (isotropic fiber distribution). The distribution of the two polymers forming the fiber, when seen in cross-section of the fiber, was alternately in the form of pie pieces of polyethylene terephthalate and polyamide 6.6, and where of a total of 16 pie pieces, 8 are made of polyethylene terephthalate and 8 of polyamide 6.6. The mass/weight relationships of polyethylene terephthalate/polyamide 6.6, in the bicomponent fiber with the 16-way pie piece subdivision in cross-section, amounts to 65/35. The bicomponent fiber has a titer of ca. 2.0 dtex. An antistatic was added to the polyamide 6.6 portion. The split fiber portion made of polyethylene terephthalate contained no further additions, as, for example, dyestuff and/or hydrophilic-rendering medium.

The spunbonded nonwoven material, not bonded up to that point, with a mass per unit area of 76 g/m² was condensed by pressing between cold rollers, for the purpose of facilitating further transportation, and was brought to a high pressure water jet-needle punching installation. The continuous filaments of the spunbonded nonwoven fabric were first intensively entangled with one another by increasing water jet pressures anywhere from 70 to 400 bar in the direction of the machine operation, and finally, toward the end of the high pressure water jet passage, split up into ultrafine microfibers with a cross-sectional piechart-shaped structure, having an average titer of 0.125 dtex. As determined by optical counting under the scanning electron microscope, the degree of splitting up was approx. 96%. A drying operation was then carried out with the dryer temperature at 180° C., and that temperature triggered a 14.2% shrinkage, which leads almost exclusively to a loss in width of the goods. In this context, the mass per unit area went up from 76 to 88.6 g/m².

Using the full bath process, the dried goods were soaked in a mixture of fluorocarbon resin set to nonionic and disperse dyestuff set to anionic. The material was then dried, the fluorocarbon resin was cross-linked, and at the same time, the disperse dyestuff was fixed in a Thermosol Process at 190° C. The take-up of dyestuff and fluorocarbon resin relative to the solid material amounted to 0.50 g/m². The relatively low dye fastness of disperse dyestuffs on the polyamide 6.6 microfiber portion of the continuous filament nonwoven fabric is not a problem, since in using it as a carrier for plasters or adhesive bandages, we are dealing with a disposable article, with not such high dye fastness requirements in that respect.

The result was a strong hydrophobic and alcohol-repellent carrier material for plasters or adhesive bandages with very high mechanical resistance to abrasion, very high tenacity, absolutely no danger of delamination (no nonwoven fabric splitting), microfiber feel, as well as good draping properties and textile quality.

The arithmetic averages of the measured test data are assembled in the following table:

| Attribute | Test Standard | Unit | Arithmetic Average |
|---|---|---|---|
| Mass Per Unit Area | EN 29073-01 | g/m² | 89 |
| Thickness | DIN 53855-01 | mm | 0.49 |
| Air Permeability at 200 Pa | EN ISO 9237 | dm³/sec m² | 150 |
| Maximum Tensile Strength - Longitudinal | EN 29073-03 | N/50 mm | 258.6 |
| Maximum Tensile Strength - Transverse | EN 29073-03 | N/50 mm | 222.3 |
| Elongation at Maximum Tensile Strength - Longitudinal | EN 29073-03 | % | 49 |
| Elongation at Maximum Tensile Strength - Transverse | EN 29073-03 | % | 52 |
| Wear-Resistance Wet at 2N and 40 Passages | Freudenberg Internal Method | Note | Page 1: 1.5 Page 2: 1.0 |
| Hydrophobicity Method of Cobb | DIN EN 20535 | g/m² | Page 1: 6 Page 2: 6 |

What is claimed is:

1. A medical bandaging material comprising a microfilament nonwoven fabric having a weight of 30 to 150 g/m² and a tear strength of >40 N/5 cm, the nonwoven fabric being made of continuous multicomponent filaments having a titer of 1.5 to 5 dtex which are melt-spun, stretched, and directly laid down to form a nonwoven fabric, wherein the continuous multicomponent filaments are split, at least to the extent of 80%, to form continuous microfilaments having a titer of 0.01 to 1.0 dtex and bonded.

2. The medical bandaging material according to claim 1, wherein the nonwoven fabric has a weight of 40 to 120 g/m², is made of continuous multicomponent filaments with a titer of 2 to 3 dtex which are melt-spun, aerodynamically stretched and directly laid down to form a nonwoven fabric, and the continuous multicomponent filaments are split at least to the extent of 80%, to form continuous microfilaments with a titer of 0.05 to 0.5 dtex and bonded.

3. The medical bandaging material according to claim 2, wherein the multicomponent filaments are prebonded before being split.

4. The medical bandaging material according to claim 1, wherein the continuous multicomponent filament is a continuous bicomponent filament made of two incompatible polymers.

5. The medical bandaging material according to claim 4, wherein the continuous multicomponent filaments have a cross-section with an orange-like multisegment structure, the segments, in alternating sequence, each including one of the two incompatible polymers or possessing a "side-by-side" structure.

6. The medical bandaging material according to claim 5, wherein the two sides of the medical bandaging material have a different segment structure.

7. The medical bandaging material according to claim 1, wherein at least one of the incompatible polymers, forming the continuous multicomponent filaments, contains amounts up to 10% by weight of an additive selected from the group consisting of dyestuffs, permanently acting antistatics, fungicides, bactericides, softeners, stabilizers, and additives influencing hydrophilic or hydrophobic properties, and mixtures thereof.

8. A method for producing the medical bandaging material according to claim 1, comprising the steps of melt-spinning the continuous multicomponent filaments, stretching the filaments and directly laying the filaments down to form a nonwoven fabric, and bonding the nonwoven fabric using high pressure fluid jets, and simultaneously splitting into continuous microfilaments with a titer of 0.01 to 1.0 dtex.

9. The method according to claim 8, further comprising the step of prebonding the filaments prior to the step of bonding.

10. The method according to claim 8, wherein the bonding and splitting of the continuous multicomponent filaments is carried out by applying high pressure fluid jets to the nonwoven fabric, at least once from each side.

11. The method according to claim 8, wherein the continuous multicomponent filaments are dyed using spin dyeing.

12. The method according to claim 8, wherein two spinning beams are used, of which one produces a continuous multicomponent filament with a pie segment structure and the other produces a continuous multicomponent filament with a side-by-side segment structure.

13. A plaster for covering small-area damage to the skin comprising the medical bandaging material according to claim 1.

14. A plaster containing active component comprising the medical bandaging material according to claim 1.

15. A plaster for covering local wounds, cuts or surgical wounds comprising the medical bandaging material according to claim 1.

16. A bandage comprising the medical bandaging material according to claim 1.

17. A wound compress comprising the medical bandaging material according to claim 1.

* * * * *